United States Patent [19]
Garrou et al.

[11] 4,080,338
[45] Mar. 21, 1978

[54] PROCESS FOR PREPARING BISPICOLYAMINE

[75] Inventors: Philip E. Garrou, Holliston; George E. Hartwell, Framingham, both of Mass.

[73] Assignee: The Dow Chemical Company, Midland, Mich.

[21] Appl. No.: 782,658

[22] Filed: Mar. 30, 1977

[51] Int. Cl.² .......................................... C07D 213/38
[52] U.S. Cl. ............................ 260/296 D; 260/296 R
[58] Field of Search ........................ 260/296 D, 296 R

[56] References Cited

PUBLICATIONS

Shcheglov et al., Chem. Abstracts, vol. 70, (11), item No. 47,237-t, Mar. 1969.
Volkova et al., Chem. Abstracts, vol. 79, (7), item No. 42,296n, Aug. 1973.
Volkova et al., Chem. Abstracts, vol. 80, (21), item No. 120,705g, May 1974.
Matsumoto et al., Chem. Abstracts, vol. 82, (23), item No. 156,097-r, Jun. 1975.

*Primary Examiner*—Alan L. Rotman
*Attorney, Agent, or Firm*—L. Wayne White

[57] ABSTRACT

Bispicolylamines are prepared by reacting (a) cyanopyridine with (b) hydrogen in the presence of a catalytic amount of (c) a palladium or carbon catalyst which has been preconditioned by contact with a reacting mixture of (a) and (b) for a time sufficient to cause said catalyst to preferentially produce bispicolylamine. The reaction is normally conducted under autogenous or superatmospheric pressure at a temperature of from about 20° to about 75° C in a lower alkanol (e.g., methanol) as the reaction medium.

8 Claims, No Drawings

PROCESS FOR PREPARING BISPICOLYAMINE

BACKGROUND OF THE INVENTION

Field of the Invention:

This is a new process for making bispicolylamine from cyanopyridines and hydrogen. Palladium on carbon is used as the catalyst.

Prior Art:

Volkova et al. teach that cyanopyridines are hydrogenated in the presence of palladium (or palladium on carbon) to form the corresponding picolylamines (i.e., aminomethylpyridines). See Volkova et al.: *Chemical Abstracts,* 79: 42296n; 80: 120705g; 81: 49570x; 83: 28065n; and 83: 113388q. Matsumoto et al. (*Chemical Abstracts,* 82: 156097r) teach that 2,6-biscyanopyridines are hydrogenated to form the corresponding 2,6-bis-(aminomethyl)pyridines as the trihydrochloride salts when the reaction is conducted over palladium on carbon using hydrochloric acid/methanol as the hydrogenation medium. These references indicate that palladium and palladium on carbon are very effective catalysts in the reaction and produce the corresponding picolylamines selectively. In view of this teaching, we were most surprised to discover that bispicolylamines could be produced selectively and in extremely high yields from the same reactant under the conditions set forth below.

SUMMARY OF THE INVENTION

We have discovered a new process for preparing bispicolylamines which comprises reacting by contacting with thorough mixing under autogenous or superatmospheric pressure (a) cyanopyridine with (b) hydrogen in the presence of a catalytic amount of (c) a palladium on carbon catalyst which has been preconditioned by contact with a reacting mixture of (a) and (b) for a time sufficient to cause said catalyst to preferentially produce bispicolylamine.

Detailed Description of the Invention

The instant process is represented by the following equation:

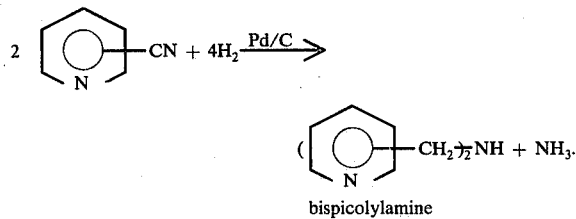

The reaction is conducted by efficiently blending the reactants and catalyst in a suitable reaction vessel under autogenous or superatmospheric pressure. The reaction is exothermic and we prefer to conduct the reaction in the presence of a liquid hydrogenation reaction medium. The lower alkanols of from 1 to 4 carbon atoms (e.g., methanol, ethanol, isopropanol, butanol, etc.) are preferred in this regard and methanol is the most preferred reaction medium.

The reaction temperature and pressure are each independently variable and may be adjusted to convenience. Preferred rates of reaction, however, have been observed at temperatures in the range of from about 20° to about 75° C. Preferred pressures range from about 50 to about 200 psig. Such superatmospheric pressures are normally achieved by using excess hydrogen. This excess positive pressure of hydrogen tends to maximize conversion of the cyanopyridine reactant and maximize product yield.

The reactants in this process are, of course, well known. Any one of the three position isomers of cyanopyridine, or a mixture thereof, can be used in the instant process but 2-cyanopyridine is the most preferred reactant. Hydrogen is a gas and is normally sparged into the reaction mixture in substantial excess, as noted above.

The catalyst used herein is a palladium on carbon which has been preconditioned by contact with a reacting mixture of cyanopyridine and hydrogen for a time sufficient to cause the catalyst to preferentially produce bispicolylamine. As indicated by the prior art, palladium on carbon catalysts initially produce picolylamine preferentially. After one or two cycles, however, we observed that the selectivity of the catalyst changes from producing picolylamine to bispicolylamine preferentially. This phenomenon is unexplained. In practice, the catalyst used herein is prepared by contacting the palladium on carbon catalyst with a reacting mixture of cyanopyridine and hydrogen while continuously monitoring the product distribution by gas chromatographic analysis. This may be conducted in a series of batch processes or by continuously flushing a stream of the reacting mixture across a catalyst bed. There are many commercial sources for palladium on carbon and such commercial catalysts are suitable for use herein. Alternatively, however, the palladium on carbon catalyst can be prepared in situ by adding a soluble palladium salt along with charcoal to the reaction medium in which case the palladium on carbon catalyst is generated in situ. The instant catalyst can be used repeatedly to effect high conversion of the reactants. After repeated usage, however, the catalytic activity tends to decrease and the reaction temperature and/or pressure are normally adjusted upward to off-set this decrease and maintain the high degree of conversion.

EXPERIMENTAL

The following experiments will further illustrate the invention.

Examples 1–4:

A series of reactions was conducted in a 500 ml Paar bomb hydrogenation apparatus. In a typical run, 2-cyanopyridine (2.0 g), 5 percent palladium on carbon (0.3 g) and 20 g of methanol were weighed into the Paar reactor which was sealed and then attached to the hydrogenator. The Paar reactor was flushed three times with hydrogen, then pressurized to 50 psig with hydrogen, and the shaker started. The reaction was monitored by pressure drop on the valve with an approximately 4 psig drop being observed in most reactions. Reaction times were selected for convenience with 6 hours being used during the day and 16 hours being used on an overnight reaction. Upon completion of the reaction, the reactor vessel was vented, the catalyst filtered, the solvent removed under reduced pressure, and the liquid residue analyzed by gas chromatography using biphenyl as an internal standard.

The results of these experiments are shown in Table I below. Each "Example" in Table I is actually a series of runs in which the reaction was conducted, the catalyst recovered and used in the subsequent run. The first run in each example was the conditioning run for the catalyst. The reaction temperature was 25° C unless otherwise indicated.

TABLE I

| Example | Pressure (psig) | Time (Hrs) | Conversion (%) | Selectivity (%) pa* | bpa* | Other |
|---|---|---|---|---|---|---|
| 1-a | 500 | 6 | 98 | 72.7 | 27.3 | |
| 1-b | 50 | 6 | 100 | 43.5 | 56.5 | |
| 1-c | 50 | 18 | 96 | 21.3 | 76.1 | 2.6 |
| 2-a | 50 | 3 | 98 | 67.7 | 32.3 | |
| 2-b | 50 | 5 | 87 | 29.5 | 61.0 | 9.5 |
| 3-a | 500 | 6 | 98 | 76 | 23 | |
| 3-b | 50 | 6 | 96 | 32 | 66 | |
| 3-c | 50 | 18 | 93 | 22.5 | 77.5 | |
| 3-d | 500 | 5 | 52 | 35 | 65 | |
| 3-e | 50 | 6 | 54 | 13 | 87 | |
| 3-f | 50 | 40 | 87 | 19 | 81 | |
| 3-g | 50 | 60 | 91 | 7 | 93 | |
| 3-h (50°) | 200 | 6 | 50 | 35 | 65 | |
| 3-i (50°) | 200 | 6 | 81 | 10 | 86 | |
| 3-j | 50 | 6 | 15 | 7 | 93 | |
| 3-k (50°) | 200 | 16 | 98 | 18 | 91 | |
| 4-a** | 50 | 6 | 90 | 85 | 15 | |
| 4-b | 50 | 16 | 100 | 33 | 66 | |

*pa and bpa represent picolylamine and bispicolylamine, respectively.
**In Examples 4a and 4b, the amount of solvent was reduced to give 30 weight percent of 2-cyanopyridine in solvent.

We claim:

1. The process for preparing bispicolylamine comprising reacting by contacting with thorough mixing under autogenous or superatmospheric pressure (a) cyanopyridine with (b) hydrogen in the presence of a catalytic amount of (c) a palladium on carbon catalyst which has been preconditioned by contact with a reacting mixture of (a) and (b) for a time sufficient to cause said catalyst to preferentially produce bispicolylamine.

2. The process defined by claim 1 wherein the reaction temperature is from about 20° to about 75° C.

3. The process defined by claim 1 wherein said reaction is conducted in a lower alkanol of from 1 to 4 carbon atoms.

4. The process defined by claim 3 wherein said lower alkanol is methanol.

5. The process defined in claim 1 wherein said process is conducted under a pressure of from about 50 to about 200 psig.

6. The process defined by claim 5 wherein said pressure is due at least in significant part to excess hydrogen.

7. The process defined by claim 1 wherein (a) is 2-cyanopyridine.

8. The process defined by claim 7 wherein the reaction temperature is from about 20° to about 75° C, the reaction pressure is from about 50 to about 200 psig and is the result of excess hydrogen, and wherein the reaction is conducted in the presence of methanol as the liquid reaction hydrogenating medium.

* * * * *

UNITED STATES PATENT AND TRADEMARK OFFICE
CERTIFICATE OF CORRECTION

PATENT NO. : 4,080,338

DATED : March 21, 1978

INVENTOR(S) : Philip E. Garrou and George E. Hartwell

It is certified that error appears in the above-identified patent and that said Letters Patent are hereby corrected as shown below:

Title Page; Column 1, line 2: "BISPICOLYAMINE" should read --BISPICOLYLAMINE--.

Title Page: Column 2, line 10: "or" should read --on--.

Column 1, line 1: "BISPICOLYAMINE" should read --BISPICOLYLAMINE--

Column 4, line 13: "in" should read --by--.

Signed and Sealed this

Fifteenth Day of August 1978

[SEAL]

Attest:

RUTH C. MASON
Attesting Officer

DONALD W. BANNER
Commissioner of Patents and Trademarks